(12) United States Patent
Yue et al.

(10) Patent No.: US 11,084,841 B1
(45) Date of Patent: Aug. 10, 2021

(54) CHITOOLIGOSACCHARIDE-N-GERANIOL DERIVATIVES, METHODS FOR PREPARING AND APPLICATION THEREOF

(71) Applicant: Jiangnan University, Wuxi (CN)

(72) Inventors: Lin Yue, Wuxi (CN); Ran Bi, Wuxi (CN); Dan Sun, Wuxi (CN); Qixing Jiang, Wuxi (CN); Bin Wang, Wuxi (CN); Xiaoli Liu, Wuxi (CN); Peipei Yu, Wuxi (CN); Zhouping Wang, Wuxi (CN); Wenshui Xia, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/020,858

(22) Filed: Sep. 15, 2020

(30) Foreign Application Priority Data

Mar. 24, 2020 (CN) .......................... 202010213943.8

(51) Int. Cl.
*C07H 15/12* (2006.01)
*C07H 1/06* (2006.01)

(52) U.S. Cl.
CPC ............... *C07H 15/12* (2013.01); *C07H 1/06* (2013.01)

(58) Field of Classification Search
None
See application file for complete search history.

(56) References Cited

PUBLICATIONS

Yue, Carbohydrate Polymers 176 (2017) 356-364. (Year: 2017).*

* cited by examiner

*Primary Examiner* — Layla D Berry
(74) *Attorney, Agent, or Firm* — Idea Intellectual Limited; Margaret A. Burke; Sam T. Yip

(57) ABSTRACT

The present invention provides a chitooligosaccharide-N-geraniol derivative and a preparation method and application thereof. The degree of substitution of a chitooligosaccharide-N-geraniol derivative is from 0.26 to 0.283. The method includes dissolving oligosaccharide in dimethyl sulfoxide, dissolving geranyl bromide in dimethylformamide, and then mixing, performing a water bath reaction and adding acetone in after the water bath reaction, performing a centrifugation and collecting precipitates, performing Soxhlet extraction and vacuum drying to obtain the chitooligosaccharide-N-geraniol derivative. The present invention has the advantages of easy preparation method, low cost, simple purification method and stable properties. The chitooligosaccharide derivative has good water solubility, antibacterial activity against *Staphylococcus aureus, Escherichia coli* and other bacteria, and has good application prospect in the fields of medicine, food, cosmetics, agriculture, etc.

16 Claims, 4 Drawing Sheets

CHITOOLIGOSACCHARIDE-N-GERANIOL DERIVATIVES, METHODS FOR PREPARING AND APPLICATION THEREOF

CROSS-REFERENCE TO RELATED APPLICATION

This application claims priority from Chinese patent application number 2020102139438 filed on Mar. 24, 2020; the disclosure of which is incorporated herein by reference in its entirety.

TECHNICAL FIELD

The present invention relates to the technical field of food additives. More particularly, it relates to chitooligosaccharide-N-geraniol derivatives and a preparation method and application thereof.

BACKGROUND

With the development of food industry, in order to extend the shelf life of food and inhibit microbial contamination, the traditional physical preservative methods have no longer satisfied the requirements. Therefore, methods of adding preservatives have been applied rapidly due to the simplicity, durability and lower cost. Because the potential cumulative toxicity of chemical preservatives, abuse or overuse will lead to food safety problems, some safe, non-toxic and green natural preservatives are more favored by people in view of the living standards improvement of people and the increase of safety awareness.

Chitooligosaccharide is a kind of natural preservative extracted from animal related substances. It is provided with the characteristics of biological non-toxic, natural degradation and good biocompatibility. In addition, chitooligosaccharide also shows a certain level of antibacterial activity, which can effectively inhibit the growth of a variety of microorganisms.

Geraniol ((2E)-3,7-dimethylocta-2,6-dien-1-ol) is a monoterpene alcohol, which existed naturally in the essential oils of plants. It has a rose-like fragrance and is the main fragrance component used in essence. It is also widely used in medicine, tobacco, food ingredients and other fields. Further, it exhibits some extraordinary properties such as insecticide, antibacterial, antioxidant, anti-inflammatory and anti-cancer effects.

Since chitooligosaccharides are natural macromolecular products, chitooligosaccharides have the disadvantage of low antibacterial activity comparing to the traditional chemical preservatives while being used as an antiseptic antibacterial agent in food. Therefore, they are not widely used in food industry. In view of the foregoing drawbacks, there is a need to provide a chitooligosaccharides derivates with higher antibacterial activity.

SUMMARY OF THE INVENTION

This section aims to summarize some aspects of the embodiments of the present invention and to briefly describe some preferred embodiments. The simplification or omission may be made in this section, the abstract of the specification, and the title to avoid obscuring the purpose of this section, the abstract of the specification, and the title. Such simplification or omission may not be used to limit the scope of the present invention.

The present invention has been made in view of the above-mentioned technical drawbacks and provides a chitooligosaccharide-N-geraniol derivative and a preparation method and application thereof. The preparation method in the present invention has the advantages of simple preparation, low cost, simple purification process and stable properties. Further, the obtained chitooligosaccharide derivatives have good water solubility and good antibacterial activity against Staphylococcus aureus, Escherichia coli and other bacteria. It is provided with good application prospect in medicine, food, cosmetics and agriculture.

Accordingly, one aspect of the present invention provides a chitooligosaccharide-N-geraniol derivative having chitooligosacharide unit represented by chemical formula (I) below:

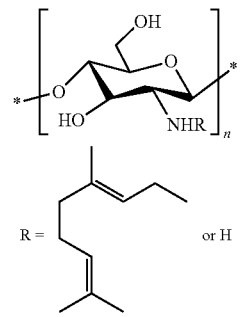

The R is independently selected from geraniol or hydrogen, n is an integer from 6 to 20, and the degree of substitution is from 0.26 to 0.283.

In one embodiment of the present invention, the molecular weight of the chitooligosaccharide is approximately 1000 Da and the deacetylation degree of the chitooligosaccharide is approximately 90%.

In one embodiment, the present invention also provides a method for preparing the chitooligosaccharide-N-geraniol derivative, which includes: dissolving oligosaccharide in dimethyl sulfoxide to obtain a first solution; dissolving geranyl bromide in dimethylformamide to obtain a second solution; mixing the first solution and second solution, adding at least one catalyst in and stirring to obtain a third solution; performing a water bath reaction to the third solution and adding acetone in after the water bath reaction to obtain a fourth solution; performing a centrifugation to the fourth solution and collecting precipitates; performing Soxhlet extraction and vacuum drying to obtain the chitooligosaccharide-N-geraniol derivative.

In one embodiment of the present invention, the mass ratio of the chitooligosaccharide and the geranyl bromide is approximately 2:1 to 2:3.

In one embodiment of the present invention, the temperature of the water bath reaction is approximately 50° C. and the reaction time of the water bath reaction is approximately 6 hours.

In one embodiment of the present invention, the catalyst is triethylamine.

In one embodiment of the present invention, the molecular weight of the chitooligosaccharide is approximately 1000 Da and the degree of polymerization is approximately from 4 to 100.

BRIEF DESCRIPTION OF THE DRAWINGS

The disclosure will become more fully understood from the detailed description given herein below for illustration only, and thus not limitative of the disclosure, wherein:

FIG. 5A is control group; FIG. 5B is chitooligosaccharide; FIG. 5C is geraniol; FIG. 5D is chitooligosaccharide-N-geraniol 1; FIG. 5E is chitooligosaccharide-N-geraniol 2; and FIG. 5F is chitooligosaccharide-N-geraniol 3.

FIG. 6A is control group; FIG. 6B is chitooligosaccharide FIG. 6C is geraniol; FIG. 6D is chitooligosaccharide-N-geraniol 1; FIG. 6E is chitooligosaccharide-N-geraniol 2; and FIG. 6F is chitooligosaccharide-N-geraniol 3.

DEFINITIONS

Figure 1:
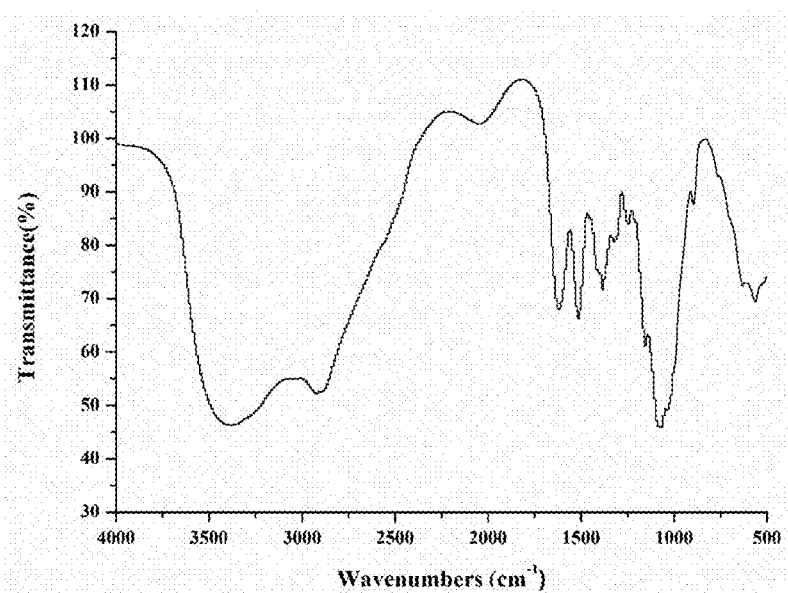
FIG. 1 shows the infrared spectrum of chitooligosaccharide.

The terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

It should be apparent to those skilled in the art that many modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "includes", "including", "comprises" and "comprising" should be interpreted as referring to elements, components, or steps in a non-exclusive manner, indicating that the referenced elements, components, or steps may be present, or utilized, or combined with other elements, components, or steps that are not expressly referenced.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In the methods of preparation described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

DETAILED DESCRIPTION

The present disclosure provides chitooligosaccharide derivatives with higher antibacterial activity, which were made by modifying the structure of chitooligosaccharides and adjusting various molecular factors. Due to the chemical reactivity of amino and hydroxyl groups in the molecular chain of chitooligosaccharides, these sites are ideal for chemical modification, and small molecular compounds with antibacterial activity can be modified on chitooligosaccharides to improve their antibacterial activities.

Figure 7:
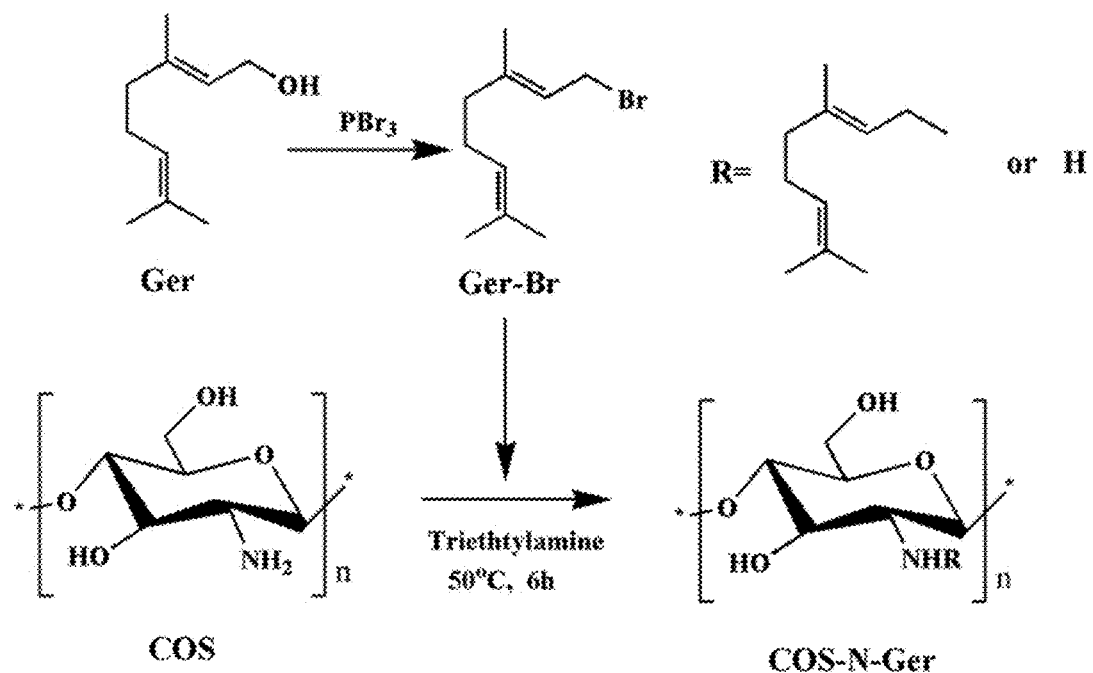
FIG. 7 shows the synthetic route of chitooligosaccharide-N-geraniol derivatives.
Figure 8:
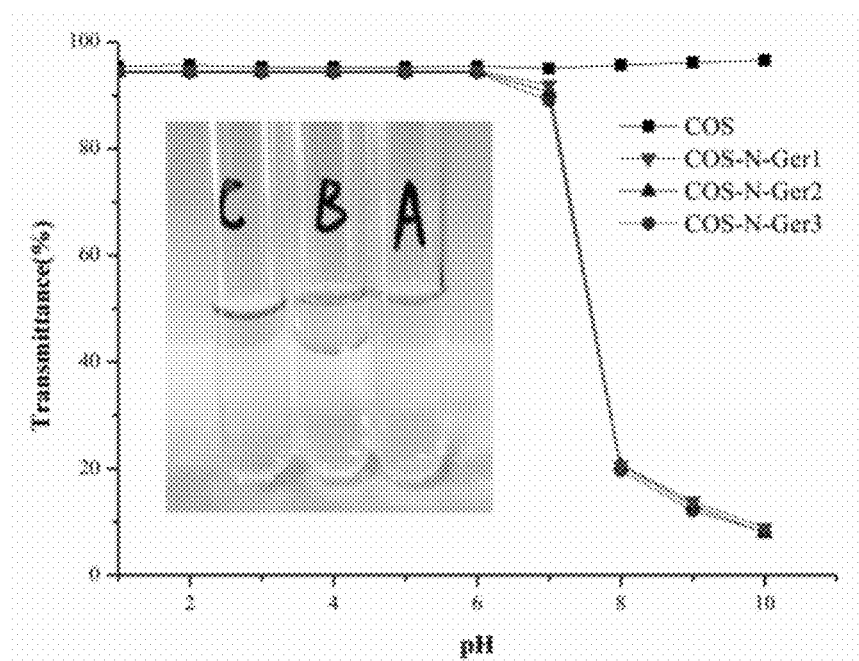
FIG. 8 shows the solubility of chitooligosaccharide and chitooligosaccharide-N-geraniol derivates at different pH, where A is chitooligosaccharide B is geraniol C is chitooligosaccharide-N-geraniol 1 dissolved in water; A (COS) and C(COS-N-Ger1) are yellow, clear and transparent solutions; B(Ger) solution appears to be stratified and the color of derivative C is darker than that of A.

The preparation method of chitooligosaccharide-N-geraniol derivatives with good water solubility and antibacterial activity are as follows: firstly, geranyl bromide is obtained by substitution reaction with phosphorus tribromide and geraniol, and geranyl bromide is reacted with two amino groups of chitooligosaccharide through alkylation reaction, and then purified to obtain chitooligosaccharide-N-geraniol derivative. The synthetic route is shown in FIG. 7.

Embodiment 1

The preparation method of chitooligosaccharide-N-geraniol derivatives includes following steps:

1. The Preparation of Geranyl Bromide:

Geraniol is dissolved in anhydrous ether with the addition of certain amount of pyridine as catalyst, and then obtain clear solution by stirring. The solution is stirred in an ice bath, and the mixture containing phosphorus tribromide and ether is dropped into the solution within 15 minutes. At the end of the reaction, the separatory funnel is used to isolate the upper organic layer and the upper organic layer is washed by water, sodium bicarbonate solution and saturated sodium chloride solution. Then, the organic layer is dried with anhydrous sodium sulfate overnight and rotary evaporation is performed to obtain the yellow syrup like product, namely geranyl bromide.

2. The Preparation of Chitooligosaccharide-N-Geraniol Derivatives:

the molecular weight of the chitooligosaccharide is approximately 1000 Da and the degree of polymerization is approximately from 4 to 7. The molar ratio of chitooligosaccharide and geranyl bromide is approximately 1:1.

Oligosaccharide is dissolved in dimethyl sulfoxide, and a certain amount of triethylamine is added as catalyst and mixed to obtain a clear solution; geranyl bromide is dissolved in dimethylformamide and is added to the chitooligosaccharide solution by constant pressure titration funnel with continuous stirring; the mixture is stirred and reacted in a water bath at 50° C. for 6 hours. Pour acetone into the mixture after the completion of the reaction so as to obtain the precipitate and collect the precipitate through centrifugation; the precipitate is extracted with petroleum ether in Soxhlet extraction device for 12 hours so as to remove the organic solvent and then is dried to obtain the crude product.

The crude product is dialyzed in ultrapure water for 24 hours and a freeze-drying is performed to obtain the pure chitooligosaccharide-N-geraniol derivatives, then analyze by IR and $^1$H NMR.

FIG. 1 shows the IR spectrum of chitooligosaccharides, where 3378 cm' is the stretching vibration absorption peak of O—H and N—H; 2962-2881 $cm^{-1}$ is the stretching vibration absorption peak of C—H; 1616 $cm^{-1}$ is the stretching vibration absorption peak of C=O; 1519 $cm^{-1}$ is the bending vibration absorption peak of $NH_2$; 1556 $cm^{-1}$ and 1071 $cm^{-1}$ are the stretching vibration absorption peaks of C—O; and 893 $cm^{-1}$ is the ring stretching vibration absorption peak.

Figure 2:
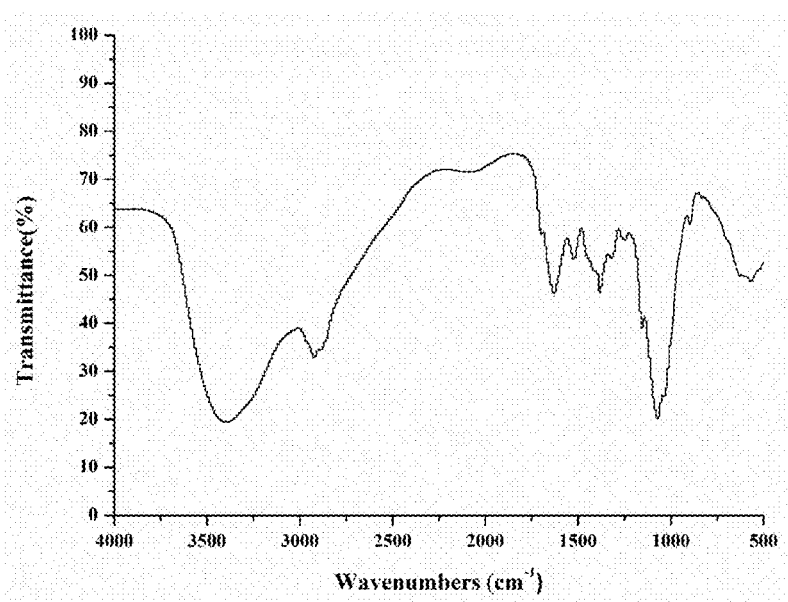
FIG. 2 shows the infrared spectrum of chitooligosaccharide derivative of one embodiment in the present invention.

FIG. 2 is the IR spectrum of the chitooligosaccharide derivatives, where the absorption peak at 1516 $cm^{-1}$ is significantly reduced; and the absorption peak at 1616 $cm^{-1}$ is shifted to 1625 $cm^{-1}$. The absorption peak becomes wider due to the substitution of $NH_2$ by geraniol, leading to overlap the vibration of C=C in geraniol and C=O in chitooligosaccharide, which confirms the successful synthesis of the target product.

Figure 3:
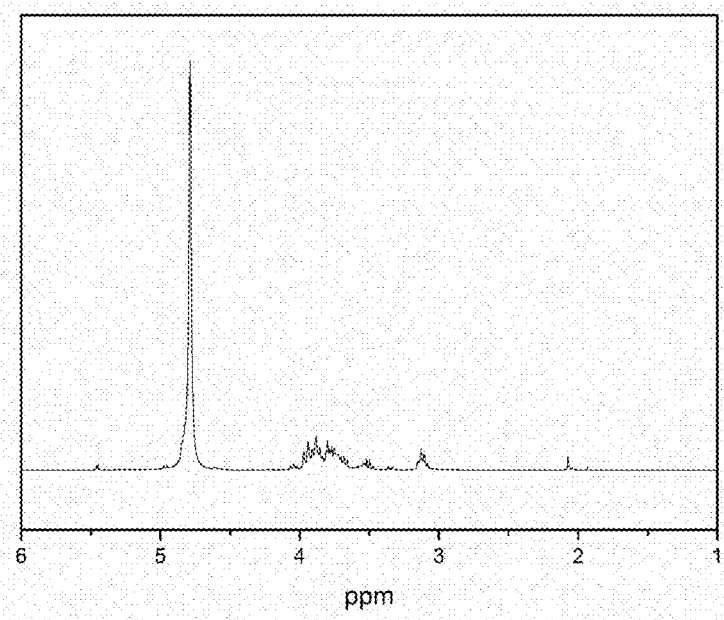
FIG. 3 shows the $^1$H NMR spectrum of chitooligosaccharide.

FIG. 3 is the $^1$H NMR diagram of chitooligosaccharide, where the peak with chemical shift at 2.07 ppm corresponds to the proton peak of $CH_3$ on the acetylamino residue. The peaks with chemical shift at 3.08-3.15 ppm correspond to the proton peak of glucosamine N, and the multiple peaks at 3.32-4.09 ppm are methylene hydrogen on glucosamine and acetylglucosamine.

Figure 4:
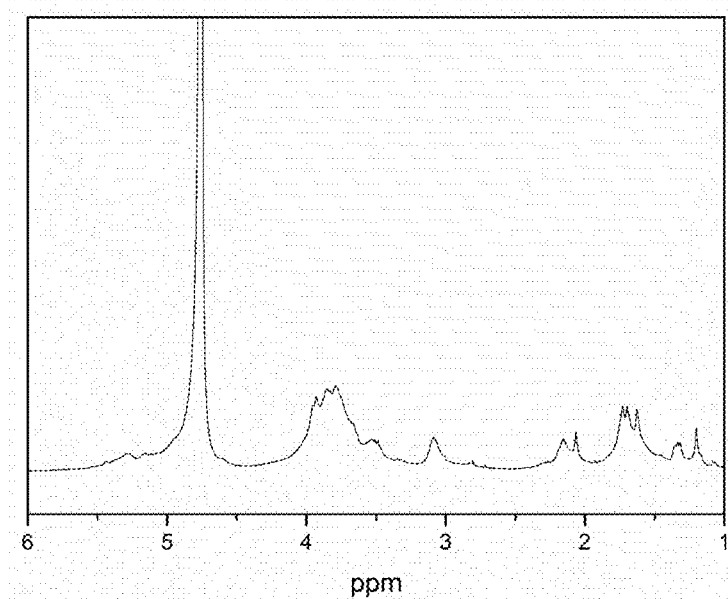
FIG. 4 shows the $^1$H NMR spectrum of chitooligosaccharide derivative of one embodiment in the present invention.
Figure 5A:
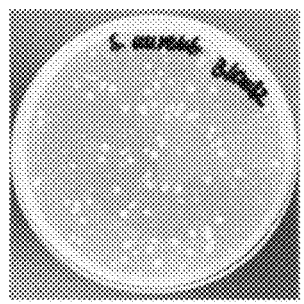
FIGS. 5A to 5F show the comparative results of inhibition tests on *Staphylococcus aureus* by chitooligosaccharide, chitooligosaccharide-N-geraniol derivatives and geraniol.
Figure 5B:
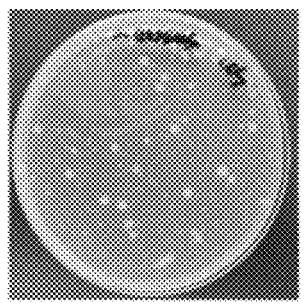
Figure 5C:
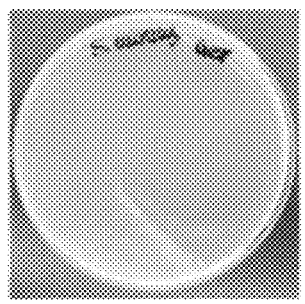
Figure 5D:
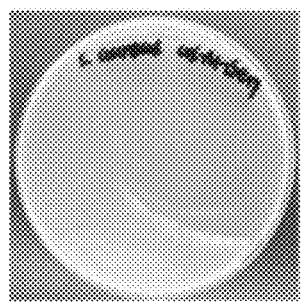
Figure 5E:
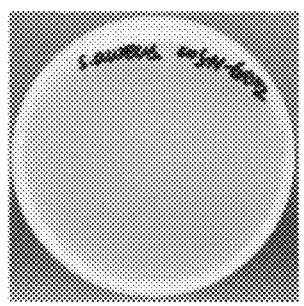
Figure 5F:
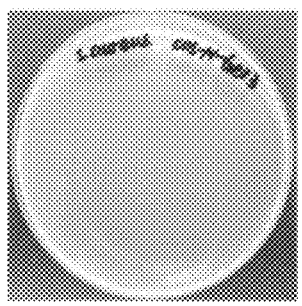

FIG. 4 is the $^1$H NMR diagram of chitooligosaccharide derivatives, where the chemical shifts of geraniol —C=C—H are at 5.15 and 5.28 ppm; the chemical shifts of methylene protons of geraniol are at 2.149 and 2.071 ppm; and the chemical shifts of geraniol $CH_3$ are at 1.731, 1.696 and 1.624 ppm, indicating the successful synthesis of the target product.

Embodiment 2

The preparation method of chitooligosaccharide-N-geraniol derivatives includes following steps:

1. The Preparation of Geranyl Bromide:

Geraniol is dissolved in anhydrous ether with the addition of certain amount of pyridine as catalyst, and then obtain clear solution by stirring. The solution is stirred in an ice bath, and the mixture containing phosphorus tribromide and ether is dropped into the solution within 15 minutes. At the end of the reaction, the separatory funnel is used to isolate the upper organic layer and the upper organic layer is washed by water, sodium bicarbonate solution and saturated sodium chloride solution. The organic layer is dried with anhydrous sodium sulfate overnight and rotary evaporation is performed to obtain the yellow syrup like product, namely geranyl bromide.

2. The Preparation of Chitooligosaccharide-N-Geraniol Derivatives:

the molecular weight of the chitooligosaccharide is approximately 1000 Da and the degree of polymerization is approximately from 4 to 7. The molar ratio of chitooligosaccharide and geranyl bromide is approximately 1:2.

Oligosaccharide is dissolved in dimethyl sulfoxide and a certain amount of triethylamine is added as catalyst and mixed to obtain clear solution; Geranyl bromide is dissolved in dimethylformamide and is added into the chitooligosaccharide solution by constant pressure titration funnel with continuous stirring; the mixture is stirred and reacted in a water bath at 50° C. for 6 hours. Pour acetone into the mixture after the completion of the reaction so as to obtain the precipitate and collect the precipitate through centrifugation; the precipitate is extracted with petroleum ether in Soxhlet extraction device for 12 hours so as to remove the organic solvent and then dried to obtain the crude product.

The crude product is dialyzed in ultrapure water for 24 hours and a freeze-drying is performed to obtain the pure chitooligosaccharide-N-geraniol derivatives.

Embodiment 3

The preparation method of chitooligosaccharide-N-geraniol derivatives includes following steps:

1. The Preparation of Geranyl Bromide:

Geraniol is dissolved in anhydrous ether with the addition of certain amount of pyridine as catalyst, and then obtain clear solution by stirring. The solution is stirred in an ice bath, and the mixture containing phosphorus tribromide and ether is dropped into the solution within 15 minutes. At the end of the reaction, the separatory funnel is used to isolate the upper organic layer and the upper organic layer is washed by water, sodium bicarbonate solution and saturated sodium chloride solution. The organic layer is dried with anhydrous sodium sulfate overnight and a rotary evaporation is performed to obtain the yellow syrup like product, namely geranyl bromide.

2. The Preparation of Chitooligosaccharide-N-Geraniol Derivatives:

the molecular weight of the chitooligosaccharide is approximately 1000 Da and the degree of polymerization is approximately from 4 to 7. The molar ratio of chitooligosaccharide and geranyl bromide is approximately 1:3.

Oligosaccharide is dissolved in dimethyl sulfoxide and a certain amount of triethylamine is added as catalyst and mixed to obtain clear solution; geranyl bromide is dissolved in dimethylformamide and added into the chitooligosaccharide solution by constant pressure titration funnel with continuous stirring; The mixture is stirred and reacted in a water bath at 50° C. for 6 hours. Pour acetone into the mixture after the completion of the reaction so as to obtain the precipitate and collect the precipitate through centrifugation; The precipitate is extracted with petroleum ether in Soxhlet extraction device for 12 hours so as to remove the organic solvent and then dried to obtain the crude product.

The crude product is dialyzed in ultrapure water for 24 hours and a freeze-drying is performed to obtain the pure chitooligosaccharide-N-geraniol derivatives.

Embodiment 4

As shown in table 1, it was found that chitooligosaccharide was completely dissolved in DMSO and partially dissolved in DMF, therefore, DMF is selected as solvent.

TABLE 1 solubility test of the products in organic solvents

| Sample | ethanol | acetone | ether | Acetic acid | DMSO | DMF |
|---|---|---|---|---|---|---|
| COS | − | − | − | ± | + | ± |
| Ger | + | + | + | + | + | + |
| COS-N-Ger1 | ± | − | − | ± | + | + |
| COS-N-Ger2 | ± | − | − | ± | + | + |
| COS-N-Ger3 | ± | − | − | ± | + | + |

Note:
+ dissolved;
± slightly dissolved;
− not dissolved;

In addition, as shown in Table 2, the productivities of COS-N-Ger1, COS-N-Ger2, and COS-N-Ger3 are from approximately 61% to 78% and degree of substitutions thereof are from approximately 0.260 to 0.283.

TABLE 2 the productivities and degree of substitutions of products

| | Reaction parameters | | produc- | Degree of |
|---|---|---|---|---|
| Samples | COS/Ger-Br | triethylamine (mL) | tivities | substitutions |
| COS-N-Ger1 | 2:1 | 0.4 | 61% | 0.260 |
| COS-N-Ger2 | 2:2 | 0.8 | 67% | 0.278 |
| COS-N-Ger3 | 2:3 | 1.2 | 78% | 0.283 |

Antibacterial Activity of Chitooligosaccharide Derivatives

Gram negative and positive bacterium (*Escherichia coli* and *Staphylococcus aureus*) are selected for the antibacterial activity test. The bacteria strain was selected to grow in LB culture medium and sub-culture to the second generation in logarithmic phase. The bacterial suspension was diluted to the required concentration ($10^5$ CFU/ml) with normal saline. Under the aseptic condition, the bacterial solution and antibacterial substance solution (mix 5 μL bacterial solution and 5 mL LB liquid medium containing 1 mg/ml antibacterial substance) were added onto the culture plate and mixed evenly. The control group was the culture plate without antibacterial substance, and then the culture plates were incubated at 37° C. for 24 hours to observe the growth of bacteria.

Figure 6A:
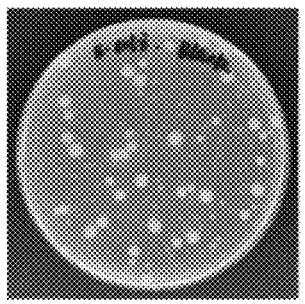
FIGS. 6A to 6F show the comparative results of inhibition tests on *E. coli* by chitooligosaccharide, chitooligosaccharide-N-geraniol derivatives and geraniol.
Figure 6B:
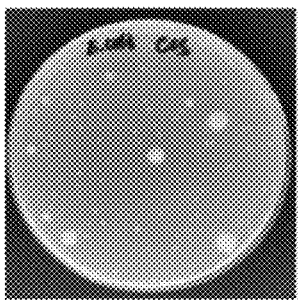
Figure 6C:
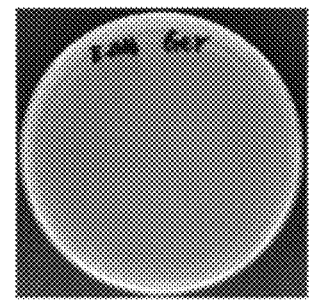
Figure 6D:
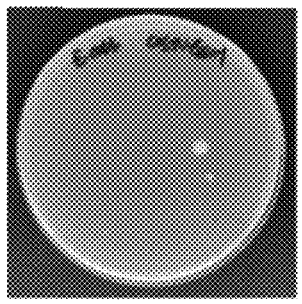
Figure 6E:
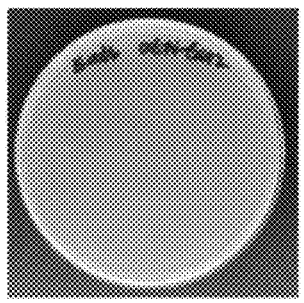
Figure 6F:
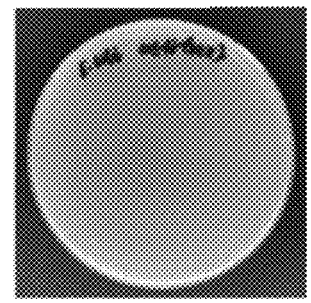

The antibacterial activities of COS, Ger and COS-N-Ger against *Staphylococcus aureus* and *Escherichia coli* are shown in FIG. 5A to 5F and FIG. 6A to 6F, respectively. Compared with the control (FIG. 5A and FIG. 6A), COS (FIG. 5B; FIG. 6B), Ger (FIG. 5C; FIG. 6C) and COS-N-Ger 1 to 3 (FIGS. 5D to 5F; FIGS. 6D to 6F) are able to inhibit *Escherichia coli* and *Staphylococcus aureus* in different levels, which suggested that the modified materials had better antibacterial activity.

Sensitivity Test of Antibacterial Derivatives to Bacteria $10^5$ CFU/ml bacterial suspension was prepared as described above. 20 to 25 mL solid medium was cooled to 50° C. and mixed with 100 μL bacterial suspension, then solidified at room temperature; punch holes (9 mm) with a puncher and mark on the substrate; add 200 μL antibacterial solution with various concentrations (1-8 mg/ml) into the wells and allow pre-diffusion at 4° C. in a refrigerator for 2 hours; Then transfer to an incubator and culture at 37° C. for 24 hours. Then, the diameter of inhibition zone of each hole was measured for three times.

As shown in table 3, the derivatives are more sensitive to *Staphylococcus aureus* than *E. coli*. Further, with the increase degree of substitution, the antibacterial activities increase gradually.

TABLE 3 the diameter of inhibition zone at different concentrations of antimicrobial substances on microorganisms

| | S. aureus | | | | E. coli | |
|---|---|---|---|---|---|---|
| Samples | 8 mg/mL | 4 mg/mL | 2 mg/mL | 1 mg/mL | 8 mg/mL | 4 mg/mL |
| COS-N-Ger1 | 13.0 ± 0.2 | 11.1 ± 0.2 | 9.5 ± 0.2 | 9 | 13.1 ± 0.2 | 9 |
| COS-N-Ger2 | 13.5 ± 0.2 | 12.0 ± 0.2 | 11.0 ± 0.2 | 10.0 ± 0.2 | 13.6 ± 0.2 | 9 |
| COS-N-Ger3 | 14.0 ± 0.1 | 12.4 ± 0.1 | 11.1 ± 0.2 | 10.6 ± 0.2 | 14.6 ± 0.2 | 9 |

Embodiment 5

The preparation method of chitooligosaccharide-N-geraniol derivatives includes following steps:

1. The Preparation of Geranyl Bromide:

Geraniol is dissolved in anhydrous ether with the addition of certain amount of pyridine as catalyst, and then obtain clear solution by stirring. The solution is stirred in an ice bath, and the mixture containing phosphorus tribromide and ether is dropped into the solution within 15 minutes. At the end of the reaction, the separatory funnel is used to isolate the upper organic layer and the organic layer is washed by water, sodium bicarbonate solution and saturated sodium chloride solution. The organic layer is dried with anhydrous sodium sulfate overnight and a rotary evaporation is performed to obtain the yellow syrup like product, namely geranyl bromide.

2. The Preparation of Chitooligosaccharide-N-Geraniol Derivatives:

the molecular weight of the chitooligosaccharide is approximately 1000 Da and the degree of polymerization is approximately from 4 to 7. The molar ratio of chitooligosaccharide and geranyl bromide is approximately 1:2.

Oligosaccharide is dissolved in dimethyl sulfoxide, and a certain amount of pyridine is added as catalyst and mixed to obtain clear solution; geranyl bromide is dissolved in dimethylformamide and is added into the chitooligosaccharide solution by constant pressure titration funnel with continuous stirring; the mixture is stirred and reacted in a water bath at 25° C. for 6 hours. Pour acetone into the mixture after the completion of the reaction so as to obtain the precipitate and collect the precipitate through centrifugation; the precipitate is extracted with petroleum ether in Soxhlet extraction device for 12 hours so as to remove the organic solvent and then dried to obtain the crude product.

The crude product is dialyzed in ultrapure water for 24 hours and a freeze-drying is performed to obtain the pure chitooligosaccharide-N-geraniol derivatives.

Meanwhile, as shown in Table 5, the productivity and degree of substitution of COS-N-Ger are from approximately 11.3% and 0.052, respectively.

TABLE 5 the productivities and degree of substitutions in one embodiment of the present invention

| Samples | Reaction parameters | | | Degree of substitutions |
|---|---|---|---|---|
| | COS/Ger-Br | pyridine (mL) | productivities | |
| COS-N-Ger | 1:2 | 0.4 | 11.3% | 0.052 |

It should be noted that the above embodiments are only used to illustrate the technical solution of the invention, rather than limitation. Although the invention is described in detail with reference to a better embodiment, those skilled in the art should understand that the technical solution of the invention can be modified or replaced equivalently without departing from the spirit and scope of the technical solution of the invention, which shall be covered in the scope of the claims of the present invention.

The invention claimed is:

1. A chitooligosaccharide-N-geraniol derivative having chitooligosaccharide unit represented by chemical formula (I):

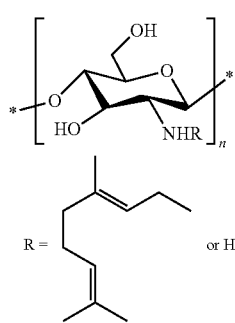

wherein R is independently selected from geraniol or hydrogen; wherein n is an integer from 6 to 20; wherein a degree of substitution is from 0.26 to 0.283.

2. The chitooligosaccharide-N-geraniol derivative of claim 1, wherein the molecular weight of the chitooligosaccharide is approximately 1000 Da and the deacetylation degree of the chitooligosaccharide is approximately 90%.

3. A method for preparing the chitooligosaccharide-N-geraniol derivative of claim 1, comprising:
dissolving chitooligosaccharide in dimethyl sulfoxide to obtain a first solution;
dissolving geranyl bromide in dimethylformamide to obtain a second solution;
mixing the first solution and second solution, adding at least one catalyst in and stirring to obtain a third solution;
performing a water bath reaction to the third solution and adding acetone in after the water bath reaction to obtain a fourth solution;
performing a centrifugation to the fourth solution and collecting precipitates;
performing Soxhlet extraction and vacuum drying to the precipitates so as to obtain the chitooligosaccharide-N-geraniol derivative.

4. A method for preparing the chitooligosaccharide-N-geraniol derivative of claim 2, comprising:
dissolving chitooligosaccharide in dimethyl sulfoxide to obtain a first solution;
dissolving geranyl bromide in dimethylformamide to obtain a second solution;
mixing the first solution and second solution, adding at least one catalyst in and stirring to obtain a third solution;
performing a water bath reaction to the third solution and adding acetone in after the water bath reaction to obtain a fourth solution;
performing a centrifugation to the fourth solution and collecting precipitates;
performing Soxhlet extraction and vacuum drying to the precipitates so as to obtain the chitooligosaccharide-N-geraniol derivative.

5. The method of claim 3, wherein the mass ratio of the chitooligosaccharide and the geranyl bromide is approximately 2:1 to 2:3.

6. The method of claim 4, wherein the mass ratio of the chitooligosaccharide and the geranyl bromide is approximately 2:1 to 2:3.

7. The method of claim 3, wherein the temperature of the water bath reaction is approximately 50° C. and the reaction time of the water bath reaction is approximately 6 hours.

8. The method of claim 4, wherein the temperature of the water bath reaction is approximately 50° C. and the reaction time of the water bath reaction is approximately 6 hours.

9. The method of claim 3, wherein the at least one catalyst is triethylamine.

10. The method of claim 4, wherein the at least one catalyst is triethylamine.

11. The method of claim 3, wherein the molecular weight of the chitooligosaccharide is approximately 1000 Da and the degree of polymerization is approximately from 4 to 100.

12. The method of claim 4, wherein the molecular weight of the chitooligosaccharide is approximately 1000 Da and the degree of polymerization is approximately from 4 to 100.

13. The method of claim 3, further comprising performing a purification reaction comprising dialyzing chitooligosaccharide-N-geraniol derivative in water for 24 hours after said vacuum drying and performing freeze drying to obtain a purified chitooligosaccharide-N-geraniol derivative.

14. The method of claim 4, further comprising performing a purification reaction, comprising dialyzing chitooligosaccharide-N-geraniol derivative in water for 24 hours after said vacuum drying and performing freeze drying to obtain a purified chitooligosaccharide-N-geraniol derivative.

15. The method of claim 3, wherein the geranyl bromide is prepared by dissolving geraniol in anhydrous ether, adding a catalyst including pyridine, and stirring to obtain a clear solution; stirring the clear solution in an ice bath, adding a mixture including phosphorus tribromide and ether to obtain a reaction solution within 15 minutes; washing, drying, and rotating evaporation to obtain the geranyl bromide.

16. The method of claim 4, wherein the geranyl bromide is prepared by dissolving geraniol in anhydrous ether, adding a catalyst including pyridine, and stirring to obtain a clear solution; stirring the clear solution in an ice bath, adding a mixture including phosphorus tribromide and ether to obtain a reaction solution within 15 minutes; washing, drying, and rotating evaporation to obtain the geranyl bromide.

\* \* \* \* \*